United States Patent
Heinze et al.

(10) Patent No.: US 8,726,745 B2
(45) Date of Patent: May 20, 2014

(54) FLUID HANDLING DEVICE WITH ULTRASOUND SENSOR AND METHODS AND SYSTEMS USING SAME

(75) Inventors: Karl R. Heinze, West Chicago, IL (US); Lee Brady, Downers Grove, IL (US); William J. Austhof, Big Rock, IL (US)

(73) Assignee: Perkinelmer Health Sciences, Inc., Waltham, MA (US)

( * ) Notice: Subject to any disclaimer, the term of this patent is extended or adjusted under 35 U.S.C. 154(b) by 365 days.

(21) Appl. No.: 11/945,193

(22) Filed: Nov. 26, 2007

(65) Prior Publication Data

US 2009/0133511 A1 May 28, 2009

(51) Int. Cl.
*B01L 3/02* (2006.01)
*G01N 1/14* (2006.01)

(52) U.S. Cl.
USPC .......... 73/863.32; 73/864.01; 73/864.24; 422/501; 422/509

(58) Field of Classification Search
USPC .......... 73/863.31–863.33, 864–864.24; 422/500–515, 99, 100
See application file for complete search history.

(56) References Cited

U.S. PATENT DOCUMENTS

| | | | | |
|---|---|---|---|---|
| 3,754,444 A | * | 8/1973 | Ure et al. | 73/863.01 |
| 3,759,667 A | * | 9/1973 | Bannister et al. | 73/864.22 |
| 4,199,013 A | | 4/1980 | Reich | |
| 4,790,183 A | | 12/1988 | Pfost | |
| 5,183,765 A | * | 2/1993 | Qureshi et al. | 436/180 |
| 5,443,791 A | * | 8/1995 | Cathcart et al. | 422/65 |
| 5,452,619 A | * | 9/1995 | Kawanabe et al. | 73/864.01 |
| 5,499,545 A | * | 3/1996 | Kimura et al. | 73/864.18 |
| 5,880,364 A | | 3/1999 | Dam | |
| 5,906,795 A | * | 5/1999 | Nakashima et al. | 422/100 |
| 5,927,547 A | | 7/1999 | Papen | |
| 6,079,283 A | | 6/2000 | Papen | |
| 6,083,762 A | | 7/2000 | Papen | |
| 6,094,966 A | | 8/2000 | Papen | |
| 6,112,605 A | | 9/2000 | Papen | |
| 6,203,759 B1 | | 3/2001 | Pelc | |
| 6,220,075 B1 | | 4/2001 | Papen | |
| 6,422,431 B2 | | 7/2002 | Pelc | |
| 6,537,817 B1 | | 3/2003 | Papen | |
| 6,592,825 B2 | | 7/2003 | Pelc | |
| 6,810,757 B2 | | 11/2004 | Carl | |

(Continued)

FOREIGN PATENT DOCUMENTS

| | | |
|---|---|---|
| EP | 0801309 | 10/1997 |
| JP | 50001018 A | 1/1975 |

(Continued)

OTHER PUBLICATIONS

International Search Report dated Mar. 10, 2009 in PCT/US2008/084502.

(Continued)

*Primary Examiner* — David A Rogers
(74) *Attorney, Agent, or Firm* — Lando & Anastasi, LLP

(57) ABSTRACT

A device comprising a sampling probe configured to sample a fluid, and an ultrasound sensor coupled to the sampling probe and configured to transmit and receive ultrasound energy, the ultrasound sensor further configured to generate a first signal by receiving ultrasound energy reflected from a fluid surface of the fluid is provided. Fluid handling systems and methods of using the fluid handling devices and systems are also disclosed.

2 Claims, 11 Drawing Sheets

(56) References Cited

U.S. PATENT DOCUMENTS

| | | |
|---|---|---|
| 6,978,689 B2 | 12/2005 | Carl |
| 7,191,647 B2 | 3/2007 | Harazin |
| 7,454,958 B2* | 11/2008 | Ellson et al. ................. 73/61.43 |
| 8,080,218 B2* | 12/2011 | Karg et al. .................... 422/501 |
| 2001/0028864 A1* | 10/2001 | Tyberg et al. ................. 422/100 |
| 2002/0108857 A1* | 8/2002 | Paschetto et al. ............. 204/457 |
| 2002/0151077 A1* | 10/2002 | Schermer et al. .............. 436/43 |
| 2003/0038071 A1* | 2/2003 | Hansen et al. ................ 210/222 |
| 2005/0092080 A1 | 5/2005 | Harazin |
| 2005/0232822 A1* | 10/2005 | Reed et al. .................... 422/100 |
| 2006/0054190 A1* | 3/2006 | Gifford et al. ................ 134/22.1 |
| 2006/0068488 A1* | 3/2006 | Anyoji et al. ................. 435/287.1 |
| 2006/0258010 A1* | 11/2006 | Safar et al. ...................... 436/43 |
| 2007/0012113 A1* | 1/2007 | Ulmer ............................. 73/618 |
| 2007/0062583 A1* | 3/2007 | Cox et al. ................. 137/565.01 |
| 2008/0102518 A1* | 5/2008 | Everett ........................ 435/288.4 |
| 2008/0111988 A1* | 5/2008 | Maroney et al. ................. 356/39 |
| 2009/0032064 A1* | 2/2009 | Gifford et al. ................... 134/18 |

FOREIGN PATENT DOCUMENTS

| | | |
|---|---|---|
| JP | 62-265570 A | 11/1987 |
| JP | 04-076670 A | 3/1992 |
| JP | 08-145763 A | 6/1996 |
| JP | 10232238 | 9/1998 |
| JP | 2000-321289 A | 11/2000 |
| JP | 2003-508782 A | 3/2003 |

OTHER PUBLICATIONS

Office Action mailed Oct. 19, 2011 by the State Intellectual Property Office of the People's Republic of China for Chinese Application No. 200880116562.5.

* cited by examiner

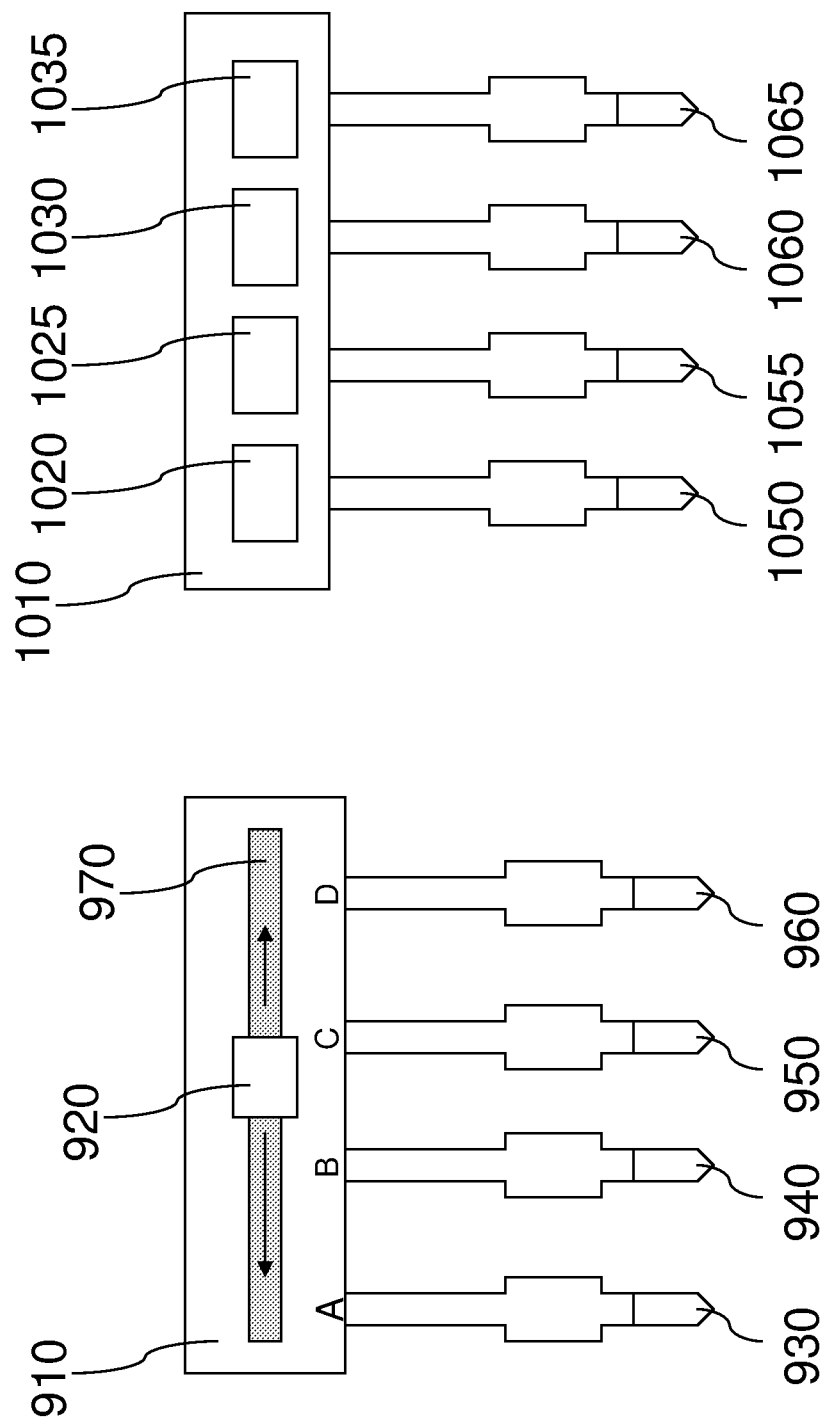

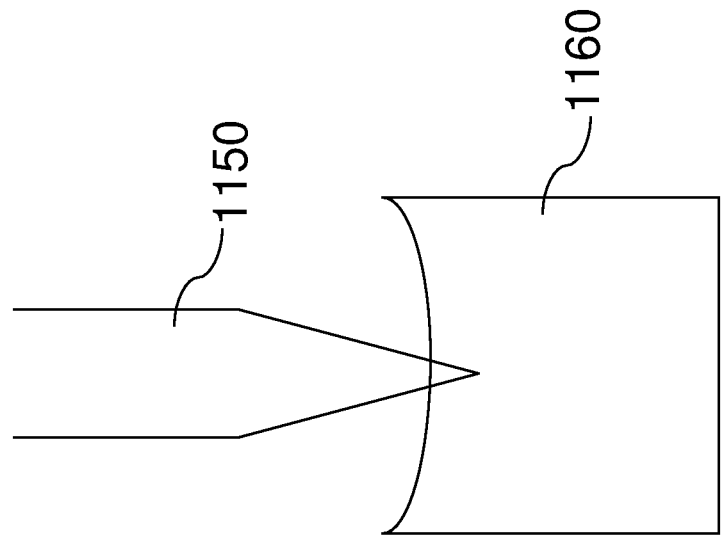
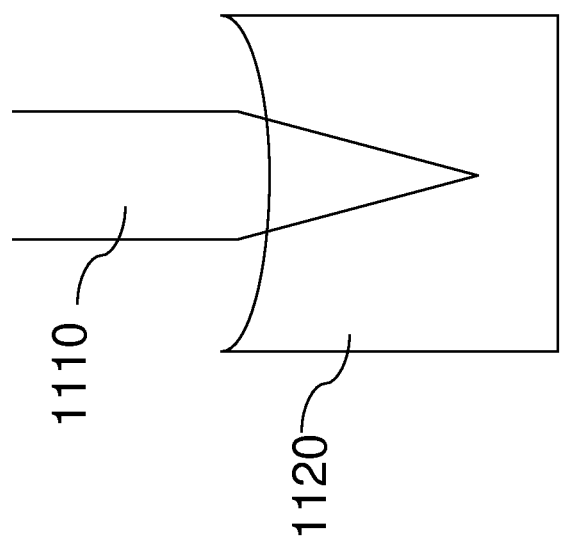

1300

FLUID HANDLING DEVICE WITH ULTRASOUND SENSOR AND METHODS AND SYSTEMS USING SAME

TECHNOLOGICAL FIELD

Examples disclosed herein relate generally to devices, methods and systems that include an ultrasound sensor for use in aspirating and/or dispensing a fluid. More particularly, certain embodiments disclosed herein relate to devices, methods and systems with an ultrasound sensor that may be used to aspirate and/or dispense non-polar fluids.

BACKGROUND

Advances in industries employing chemical and biological processes have created a need for the ability to accurately and automatically sample quantities of fluids containing chemical or biological substances for commercial or experimental use. Accuracy and reproducibility is particularly difficult where the fluid to be sampled is viscous or hydrophobic.

SUMMARY

In accordance with a first aspect, a device comprising a sampling probe configured to sample a fluid, and an ultrasound sensor coupled to the sampling probe and configured to transmit and receive ultrasound energy is provided. In some examples, the ultrasound sensor may be further configured to generate a first signal by receiving ultrasound energy reflected from a fluid surface of the fluid.

In certain embodiments, the ultrasound sensor may be further configured to generate a second signal by detecting ultrasound energy reflected from a first surface configured to receive a fluid container comprising the fluid. In certain examples, the device may further comprise a controller electrically coupled to the ultrasound sensor and configured to receive the first signal and the second signal. In some examples, the device may further comprise a system fluid reservoir fluidically coupled to the sampling probe, and the sampling probe may be further configured to dispense a fluid from the system fluid reservoir through the sampling probe. In certain examples, the device may further comprise a pump fluidically coupled to the sampling probe and configured to provide a negative pressure to aspirate sample in the sampling probe. In other examples, the pump may be further configured to provide a positive pressure to dispense aspirated sample from the sampling probe. In additional examples, the device may further comprise a moveable support configured to receive the sampling probe and the ultrasound sensor. In certain embodiments, the sampling probe may be configured to receive a sampling element. In other examples, the device may comprise a plurality of sampling probes, wherein the ultrasound sensor is configured to be moveable and be used with each of the plurality of sampling probes. In some examples, the device may comprise a plurality of ultrasound sensors, wherein one of the plurality of sampling probes is configured for use with one of the plurality of ultrasound sensors.

In accordance with another aspect, a fluid handling system is provided. In certain examples, the fluid handling system comprises a surface configured to receive a fluid container, at least one moveable support, a sampling probe coupled to the at least one moveable support, a pump fluidically coupled to the sampling probe, an ultrasound sensor coupled to the a least one moveable support and configured to generate a first signal by receiving ultrasound energy reflected from a fluid surface of a fluid in the fluid container, and a controller configured to receive the first signal and to move the at least one moveable support in response to the first signal to aspirate a fluid from the fluid container.

In certain embodiments, the ultrasound sensor of the fluid handling system may be further configured to generate a second signal by detecting ultrasound energy reflected from the surface configured to receive the fluid container, and the controller may be further configured to move the moveable support in response to the first signal and the second signal. In some examples, the fluid handling system may further comprise a plurality of sampling probes coupled to the moveable support. In other examples, the fluid handling system may further comprise a plurality of ultrasound sensors coupled to the moveable support, in which each of the plurality of sampling probes is configured for use with one of the plurality of ultrasound sensors. In some embodiments, the fluid handling system may further comprise a system fluid reservoir fluidically coupled to the sampling probe. In additional examples, the fluid handling system may further comprise a valve coupled to the system fluid reservoir and the sampling probe, the valve configured to actuate to permit fluid to be dispensed from the system fluid reservoir through the sampling probe. In other examples, the moveable support of the fluid handling system may comprise a three-axis robotic arm. In certain examples, the sampling probe of the fluid handling system may comprise an end configured to receive a sampling element. In some examples, the sampling probe may be configured to eject the sampling element after dispensing the aspirated fluid.

In accordance with an additional aspect, a fluid handling system comprising a plurality of sampling probes is provided. In certain examples, the system comprises a surface configured to receive a fluid container, at least one moveable support, a plurality of sampling probes each coupled to the at least one moveable support, a plurality of pumps, wherein one of the plurality of pumps is fluidically coupled to one of the plurality of sampling probes, a plurality of ultrasound sensors coupled to the at least one moveable support, wherein one of the plurality of ultrasound sensors is coupled to one of the plurality of sampling probes, and each of the ultrasound sensors may be configured to generate a first signal by receiving ultrasound energy reflected from a fluid surface of a fluid in the fluid container, and a controller configured to receive the first signal and to move the at least one moveable support in response to the first signal to aspirate a fluid from the fluid container.

In certain embodiments, the ultrasound sensor may be further configured to generate a second signal by detecting ultrasound energy reflected from the surface configured to receive the fluid container, and the controller may be further configured to move the moveable support in response to the first signal and the second signal. In additional examples, the fluid handling system may further comprise a system fluid reservoir fluidically coupled to the sampling probe. In some examples, the valve may be further coupled to the system fluid reservoir. In other examples, the moveable support of the fluid handling system comprises a three-axis robotic arm. In certain examples, the sampling probe may comprise an end configured to receive a sampling element. In some examples, the sampling probe may be configured to eject the sampling element after dispensing the aspirated fluid.

In accordance with another aspect, a method of sampling a fluid is provided. In certain examples, the method comprises determining a distance from a sampling probe to a fluid surface by providing ultrasound energy from an ultrasound sensor to the fluid surface of a fluid, and receiving reflected ultrasound energy from the fluid surface using the ultrasound sensor to determine the distance between the sampling probe and the fluid surface, and moving the sampling probe an effective distance into the fluid to aspirate a selected volume of fluid into the sampling probe.

In certain embodiments, the method may further comprise providing ultrasound energy to a surface configured to receive a fluid container comprising the fluid and receiving reflected ultrasound energy from the surface using the ultrasound sensor to determine a distance from the sampling probe to the surface. In certain examples, the method may further comprise dispensing the aspirated fluid in a second fluid container. In some examples, the method may further comprise dispensing a system fluid through the sampling probe from a system fluid reservoir fluidically coupled to the sampling probe.

In accordance with an additional aspect, a method of sampling a hydrocarbon fluid is disclosed. In certain examples, the method comprises determining a distance from a sampling probe to a hydrocarbon fluid surface by providing ultrasound energy from an ultrasound sensor to the hydrocarbon fluid surface, and receiving reflected ultrasound energy from the hydrocarbon fluid surface using the ultrasound sensor to determine the distance between the sampling probe and the hydrocarbon fluid surface. In certain embodiments, the method may further comprise determining a sampling distance to move the sampling probe into the hydrocarbon fluid to aspirate a selected volume of fluid from the hydrocarbon fluid in the sampling probe, wherein the sampling distance is configured to aspirate the selected volume while minimizing a depth at which the sampling probe is moved into the hydrocarbon fluid.

Additional features, aspects, examples and embodiments of the technology are described in more detail below.

BRIEF DESCRIPTION OF THE FIGURES

Certain embodiments are described in more detail below with reference to the figures in which:

FIG. 8 is a device comprising a single ultrasound sensor and a plurality of sampling probes, in accordance with certain examples;

FIG. 9 is a device comprising a plurality of sampling probes and a plurality of ultrasound sensors with each of the plurality of ultrasound sensors being coupled to a respective one of the plurality of sampling probes;

FIGS. 10A and 10B are illustrations of sampling probes that have been moved into a fluid, in accordance with certain examples;

Figure 1:
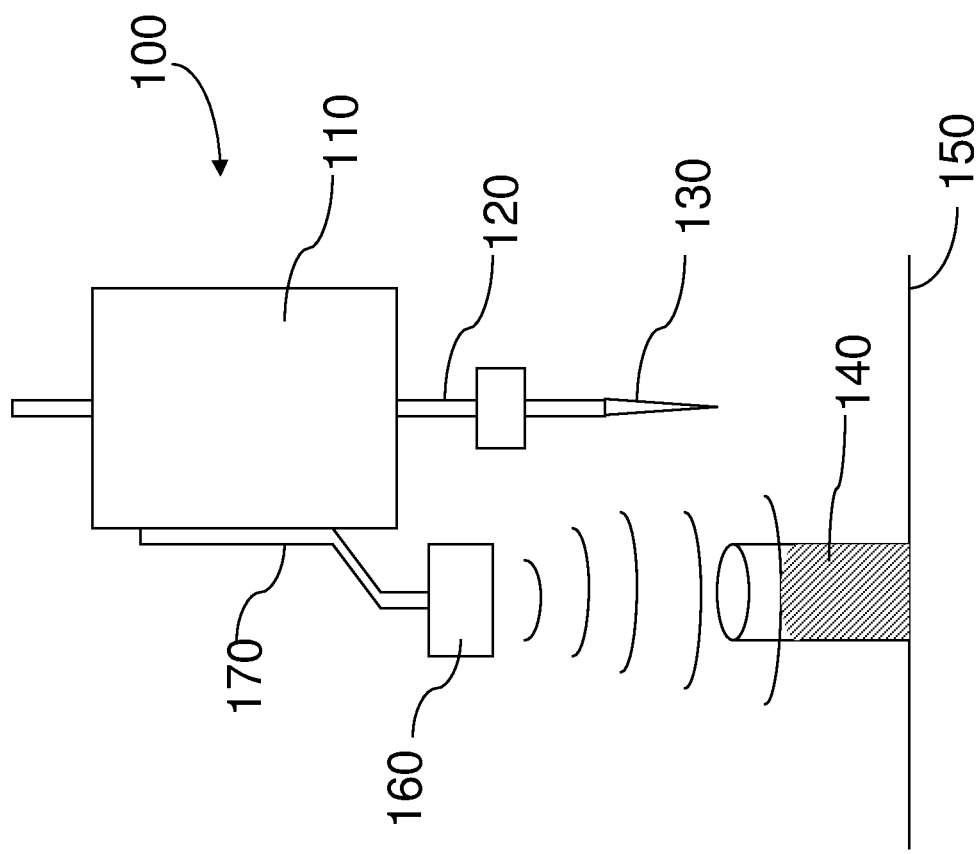
FIG. 1 is an illustration of a device that comprises a sampling probe and an ultrasound sensor, in accordance with certain examples.

Unless otherwise clear from the context, the use of the terms "top" and "bottom" is arbitrary and for illustrative purposes only, and the devices and systems disclosed herein may be used in any orientation to sample a fluid. In addition, certain dimension, features, components and the like may have been enlarged, distorted or otherwise shown in a non-proportional or non-conventional manner to facilitate a better understanding of the technology disclosed herein. If one or more components of the figures is referred to as being "coupled to" another component, the components may be joined or connected directly without any intervening parts, or structures or the components may be joined or connected through one or more additional and intervening parts or structures.

DETAILED DESCRIPTION

Certain features, aspects and examples of the technology disclosed herein provide significant advantages over existing systems including, but not limited to, automated, accurate and/or precise sampling of non-viscous and viscous fluids, such as hydrocarbons.

In accordance with certain examples, the devices, systems and methods disclosed herein advantageously utilize one or more ultrasound sensors to increase the overall accuracy and precision of sampling of a fluid. The term "sampling," as used herein includes both aspirating and dispensing and other fluid handling operations that may be performed using the fluid handling systems disclosed herein. In certain embodiments, a single ultrasound sensor may be used, whereas in other embodiments each sampling probe may include a corresponding ultrasound sensor with each ultrasound sensor configured to operate independently of the other ultrasound sensors. In certain examples, the ultrasound sensor may be used, at least in part, to assist in controlling the distance a sampling probe is lowered into a fluid. By controlling how far the sampling probe is lowered into a fluid, the amount of fluid coated or adsorbed on the outside of the sampling probe may be reduced to increase the overall sampling accuracy of the fluid.

In some examples, the ultrasound sensor may be used to receive reflected ultrasound energy and to generate a signal in response to the reflected ultrasound energy. In certain examples, the ultrasound energy may be used to determine a distance from a sampling probe end to a fluid surface. In other examples, one or more other ultrasound measurements may be performed to calibrate the system and/or to assist in determination of a distance to a fluid surface. Such other measurements include, but are not limited to, calibration of the system such that the starting distance to a surface configured to receive a fluid container is known. In embodiments where the sampling probe starts at a known or fixed position prior to sampling, such additional measurement may not be desirable as they may increase the overall sampling time. In certain examples, the ultrasound sensor may provide the ultrasound energy and then receive reflected ultrasound energy, whereas in other examples one ultrasound sensor may be used to provide the ultrasound energy and a second ultrasound sensor may be used to detect the reflected ultrasound energy.

In accordance with certain examples, the systems, devices and methods disclosed herein that include the use of an ultrasound sensor may be used to determine or select a desired distance to lower a sampling probe into fluid. In certain existing methods, the sampling probe may be lowered a substantial distance into a fluid container to ensure the sampling probe contacts the fluid. In instances where the fluid is viscous or hydrophobic, however, the fluid may adhere to or otherwise stick to the outer surface of the sampling probe. Such undesired sticking reduces the overall accuracy of the sampling probe as fluid which is stuck to the outside of the sampling element may be undesirably dispensed or drop. This sticking is particularly detrimental where the sampling volume is on the order of a few microliters, because sticking of even a small amount of fluid to the sampling element can introduce large sampling errors. Using an ultrasound sensor, the distance to a surface of a fluid may be determined, and the sampling element may be lowered into the fluid a suitable distance to aspirate a desired volume of fluid into the sampling element while reducing or minimizing unnecessary contact between the outer surface of the sampling element and the fluid. The fluid to be sampled may include particulate matter, may be polar or non-polar, may be viscous or relatively non-viscous, may be colored or colorless, may be transparent or opaque or may include other physical or chemical properties. Such devices, systems and methods are particularly useful for viscous fluids such as, for example, hydrocarbon fuels (e.g., gasoline, diesel fuel, heating oil, etc.), lubricants, oils, waxes, glycols, aromatics, phenols, starch or sugar solutions, natural products (e.g., honey, molasses, peanut oil and other plant oils), ethers, basic solutions (e.g., 30% NaOH), acidic solutions (e.g., 60-100% $H_2SO_4$), tars and other viscous fluids. In some examples, the devices, systems and methods disclosed herein are particularly useful for fluids whose viscosity is greater than or equal to 50 cPs. While the devices, systems and methods disclosed herein may be used in sampling of viscous fluids, the increased accuracy and precision provided by the devices, systems and methods disclosed herein also permits their use with non-viscous fluids such as, for example, aqueous based solutions, e.g., fluids having a viscosity of less than or equal to 50 cPs.

In certain examples, the devices, systems and methods disclosed herein may be used to aspirate a selected volume of fluid. Aspiration refers to drawing, sucking or otherwise moving the fluid into a sampling probe. The exact volume aspirated into the sampling probe may vary depending on the intended end use of the fluid, e.g., chemical analysis, array fabrication and the like. In some examples, the volume of fluid aspirated into the sampling probe may vary from about 0.1 microliters to about 10 milliliters, more particularly, about 1 microliters to about 1 milliliters, e.g., about 1 mL. Subsequent to aspiration, a selected amount of the fluid drawn into the sampling probe may be dispensed into a desired container or onto a desired surface. In some examples, the entire fluid volume in the sampling probe may be dispensed into a container, whereas in other examples, a volume smaller than the total volume aspirated into the sampling probe may be dispensed. In certain examples, the sampling probe may also be used to dispense a system fluid into a desired container or on a desired surface. In some examples, the system fluid may be used to flush the sampling probe to ensure all the aspirated fluid has been removed from the sampling probe. Additional methods of aspirating and dispensing using the devices, systems and methods disclosed herein will be readily selected by the person of ordinary skill in the art, given the benefit of this disclosure.

In accordance with certain embodiments, a sampling probe that is coupled to an ultrasound sensor may be used to aspirate and/or dispense a fluid. An illustrative sampling probe coupled to an ultrasound sensor is shown in FIG. 1. The device 100 includes a moveable support 110 coupled to a sampling probe 120, which may be disposed centrally within the moveable support 110. The sampling probe 120 may be coupled to, or may include, a sampling element 130, which may be fixed or detachable. In certain embodiments, the sampling element 130 may take the form of a pipette tip that includes a hollow central cavity which can receive a fluid upon application of a negative pressure, e.g., aspiration, and eject the fluid upon application of a positive pressure, e.g., dispensing. Various sizes of sampling elements may be used to provide for different sampling volumes. During operation of the device 100, a selected volume of fluid may be aspirated into the sampling element 130 from a fluid source, such as a fluid container 140 resting on a surface 150. Subsequent to aspiration, the device 100 may dispense the aspirated fluid into another receptacle or container (not shown).

In certain examples, the sampling probe 120 may be lowered by a selected distance into the fluid container 140 prior to aspiration of the fluid into the sampling element 130. The distance that the sampling probe 120 is lowered may be assisted by an ultrasound sensor 160 coupled to the sampling probe 120. The ultrasound sensor 160 may be configured to provide ultrasonic energy to a surface such as, for example, a fluid surface of a fluid in the fluid container 140, and to receive reflected energy from the fluid surface to determine the distance the sampling probe is from the fluid surface. In some examples, the ultrasonic energy may be provided in the form of a pulse, and the reflected energy, e.g., an echo may be received. The time it takes from the pulse transmission to receipt of the echo may be used to determine a distance a sampling element is positioned from a fluid surface. By ascertaining or determining the difference between the end of the sampling element 130 and the fluid surface of the fluid in the fluid container 140, the sampling probe 120 may be lowered a suitable distance into the fluid such that a selected or desired amount of fluid may be aspirated into the sampling element 130. By controlling the distance the sampling probe 120 is lowered into the fluid, the amount of fluid that may coat or otherwise be adsorbed to the outside of the sampling element 130 may be reduced to increase the overall accuracy and precision of aspiration using the device 100.

In accordance with certain examples, during operation of the ultrasound sensor 160, the distance to a fluid level in a fluid container may be determined by calibrating the sensor using a known distance. For example, the ultrasound sensor 160 may provide ultrasonic energy to the surface 150 whose distance from the sampling element 130 of the sampling probe 120 is known. Such known distance may be stored in a calibration routine which, when implemented by a suitable controller, can cause the moveable support 110 to park or position itself a known distance from the surface 150. Reception of the reflected energy by the ultrasound sensor may result in generation of a signal, e.g., a calibration signal, which may be sent to a controller. The calibration signal may be stored in the controller and used to determine a distance to lower the sampling probe 120. For example, a signal may be generated in response to detection of a fluid level in a fluid container, e.g., a fluid level signal may be generated by providing ultrasound energy and receiving ultrasound energy reflected by the surface of the fluid. The calibration signal may be used with, or compared to, the fluid level signal to determine how far the sampling probe should be lowered to contact the fluid in the fluid container. In an alternative configuration, a calibration curve may be generated or used such that the reflected ultrasonic energy at many different distances is used to determine the distance to lower a sampling probe in response to a fluid level signal. Additional methods using an ultrasound sensor to detect a fluid level and to lower a sampling probe into the fluid a suitable or selected distance will be readily selected by the person of ordinary skill in the art, given the benefit of this disclosure.

Figure 2:
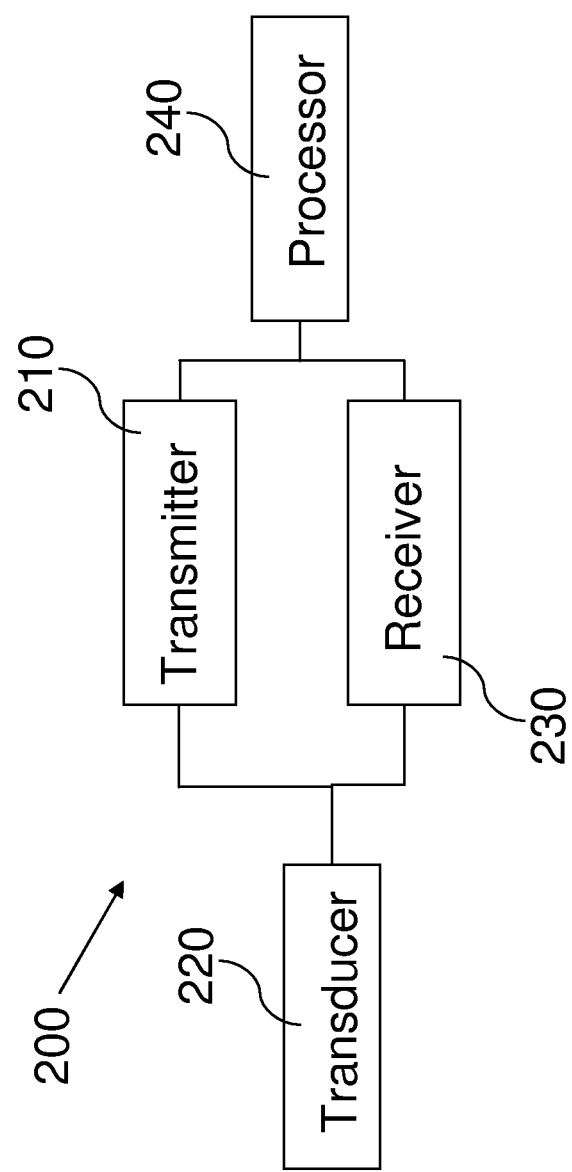
FIG. 2 is a block diagram of an ultrasound sensor, in accordance with certain examples.

In accordance with certain examples, the exact frequency of ultrasound energy that may be used in the devices, systems and methods disclosed herein may vary depending on the fluid to be sampled, the type of ultrasound sensor and the like. In certain embodiments, the ultrasound sensor may provide energy having a frequency between about 20 kHz to about 200 MHz, e.g., about 250 kHz to about 400 kHz. In some examples, an ultrasound sensor is selected such that it is effective to detect distances between about 1-10 inches, more particularly about 2-8 inches. However, by increasing or decreasing the power of the ultrasound energy transmitted by the ultrasound sensor, it may be desirable to increase or decrease, respectively, the distance the ultrasound sensor is mounted from a surface or fluid. In certain embodiments, the ultrasound sensor may provide a cone of ultrasonic energy such that energy from one ultrasound sensor does not interfere with ultrasonic energy from another ultrasound sensor. A block diagram of an illustrative ultrasound sensor is shown in FIG. 2. The ultrasound sensor 200 comprises a transmitter 210 that provides ultrasound energy to a transducer 220, e.g., one that may include a piezoceramic crystal(s). Numerous different types of transducer geometries may be used to provide a desired energy profile. The transducer 220 provides the ultrasonic energy from the transmitter 220 to a surface. As energy is reflected back from the surface and is incident on transducer 220, the reflected signals are provided to a receiver 230. The receiver 230 may receive reflected energy from a surface or fluid and provide the type, level or wavelength of reflected energy to the processor. The receiver 230 may be electrically coupled to a processor 240, which may include one or more lists or algorithms to store the reflection data and/or to calculate a distance using the reflection data and/or the transmission data. The processor 240 may also be configured to send a signal to effectuate movement of the moveable support such that a sampling probe is lowered a desired distance into a fluid. Other alternatives for providing a signal that represents a distance to a surface, or for providing data to a processor for determination of a distance, will be readily selected by the person of ordinary skill in the art, given the benefit of this disclosure. Illustrative ultrasound sensors suitable for use in the fluid handling systems disclosed herein include, but are not limited to, those commercially available from Baumer Electric AG (Switzerland) such as, for example, Model No. UNDK10U6914.

In certain embodiments, it may be desirable to include shielding around a device or system that includes an ultrasound sensor. Such shielding may prevent or reduce interference from external sound waves and may prevent or reduce the ultrasound energy from interfering with other equipment or devices near the ultrasound sensor. The shielding may be attached directly to the ultrasound sensor and, for example, surround part of the ultrasound sensor, or the shielding may be external and not attached directly to the ultrasound sensor. Illustrative ultrasound shielding may be made from, or may include, metal foils, foams, and other metals that can absorb ultrasonic energy.

Figure 3:
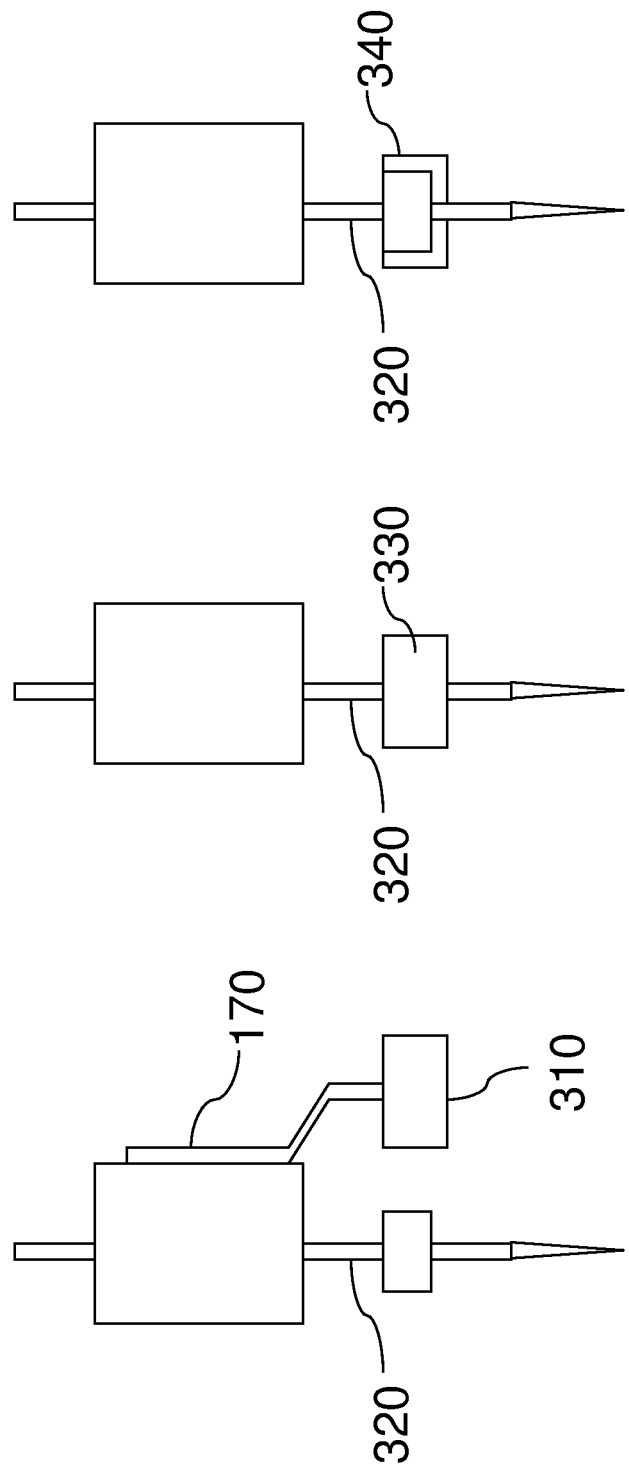
FIGS. 3A-3C are illustrations of varying placement of an ultrasound sensor with respect to the position of a sampling probe, in accordance with certain examples.

In certain embodiments, the ultrasound sensor may be coupled to the sampling probe using one or more fittings or attachments. In certain examples, an outrigger bar 170 (see FIG. 1) may be used to couple the ultrasound sensor 160 to the moveable support 110 and/or the sampling probe 120. In certain examples, the ultrasound sensor 160 may be placed in any position, relative to the position of the sampling probe 120 that permits use of the ultrasound sensor 160 to transmit and receive ultrasound energy to a surface. In the illustration shown in FIG. 1, the outrigger bar 170 positions the ultrasound sensor 160 to the left of the sampling probe 120. As shown in FIGS. 3A-3C, an ultrasound sensor 310 may be placed to the right of a sampling element 320 (FIG. 3A), an ultrasound sensor 330 may be placed in front of a sampling element 320 (FIG. 3B), an ultrasound sensor 340 may be placed behind a sampling element 320 (FIG. 3C) or an ultrasound sensor may be placed in any position between these illustrative positions. In some examples, the ultrasound sensor may be configured with a through-hole or aperture configured to receive the sampling element such that the body of the ultrasound sensor surrounds a portion of the sampling probe body. Placement of the ultrasound sensor relative to the placement of the sampling probe is not limited. Similarly, placement of the ultrasound sensor relative to a surface or a fluid is not limited provided that energy transmitted by the ultrasound sensor may contact the surface or the fluid. In certain embodiments, the vertical distance from the ultrasound sensor to a surface or a fluid may be between about 1-9 inches, more particularly about 2-7 inches, e.g., about 3-6 inches. In addition, in certain embodiments the moveable support 110 may be moved in a vertical direction to increase or decrease the distance the ultrasound sensor is from a surface or a fluid surface.

In certain examples, one or more of the ultrasound sensors may be mounted or otherwise coupled to a gantry system or an independent moveable support separate from support used to mount the sampling probes. This moveable support may move with the sampling probes or may move independently with the sampling probes. Suitable devices for mounting and controlling ultrasound sensors that are mounted to a separate moveable support will be readily selected by the person of ordinary skill in the art, given the benefit of this disclosure.

Figure 4:
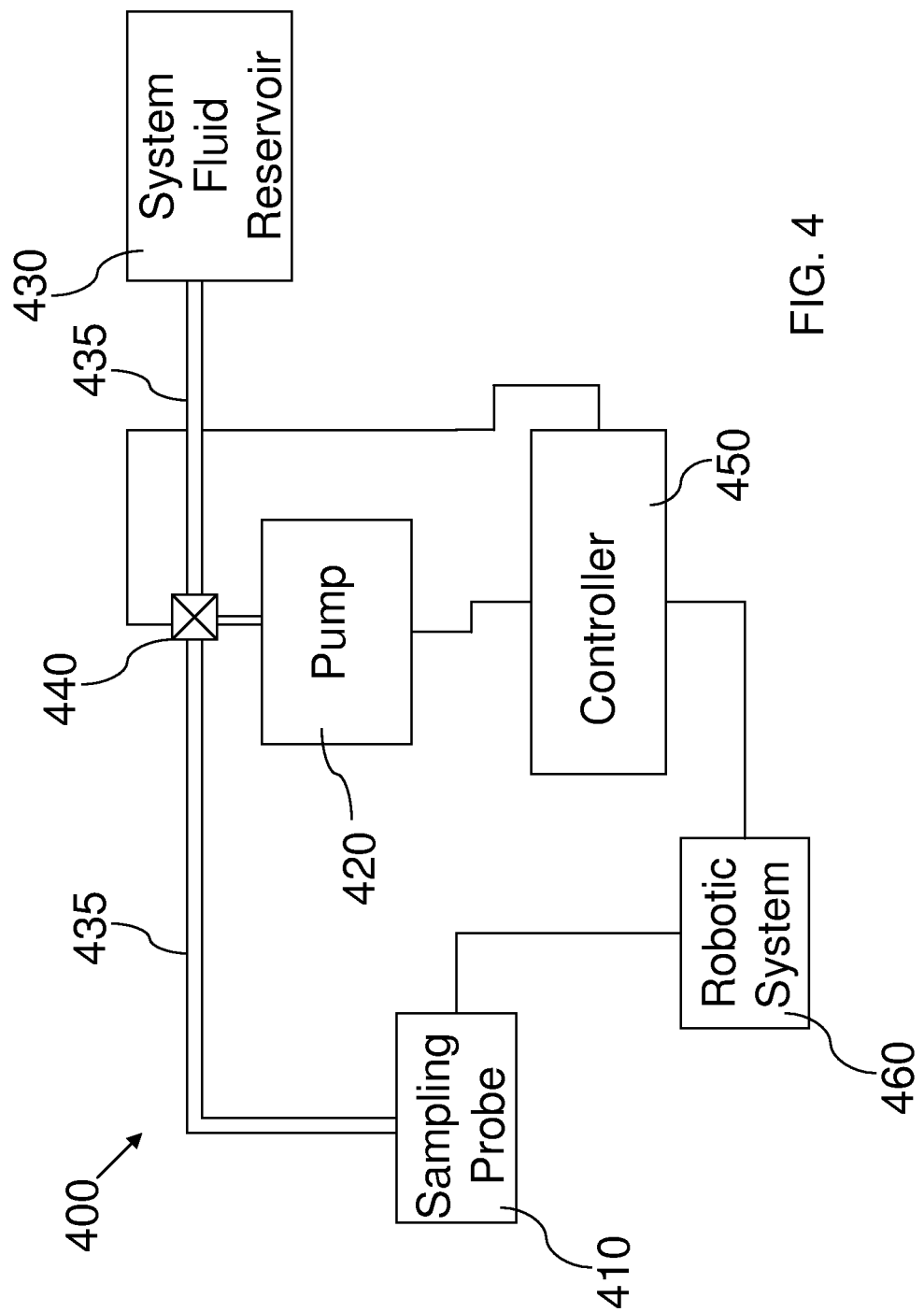
FIG. 4 is a block diagram of a fluid handling system in accordance with certain examples.

In accordance with certain examples, one or more of the sampling probes disclosed herein, e.g., one that includes an ultrasound sensor, may be used in a fluid handling system. A block diagram of an illustrative fluid handling system is shown in FIG. 4. The fluid handling system 400 includes a sampling probe 410 fluidically coupled to a pump 420 and a system fluid reservoir 430 through a valve 440 and a fluid conduit 435. A system controller 450 is electrically coupled to the sampling probe 410, the pump 420 and the valve 440 to control aspiration and dispensing of a fluid from or to a fluid container and/or to control dispensing of fluid from the system fluid reservoir 430. A robotic system 460 is mechanically coupled to the sampling probe 410 and is operative to move the sampling probe 410 in three directions, e.g., in an x-axis, y-axis and/or z-axis direction. Such robotic system 460 is referred to in certain instances herein as a 3-axis robotic system. The fluid handling system 400 may aspirate a selected volume of a fluid into the sampling probe 410, may dispense the aspirated fluid and/or may dispense a selected volume of a system fluid from the system fluid reservoir 430 through the sampling probe 410. The sampling probe 410 typically includes, or is coupled to, an ultrasound sensor which itself may be electrically coupled to the controller 450.

Figure 5:
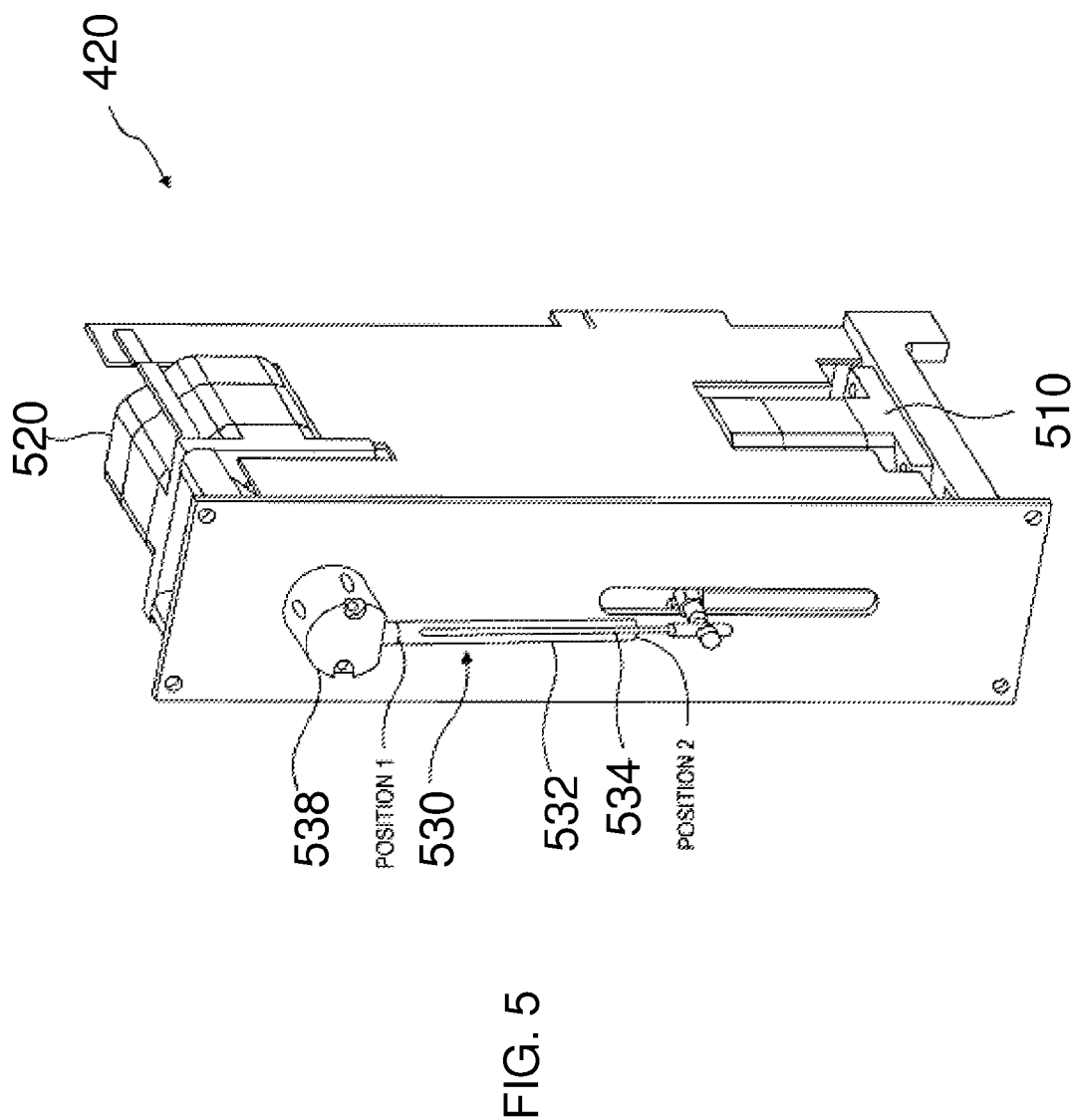
FIG. 5 is an illustration of a pump, in accordance with certain examples.

In certain embodiments, the pump 420 may be configured as a syringe pump. One or more components of the syringe pump may be operative to move or be moved in discrete steps such that a desired volume will be aspirated into the sampling probe, dispensed from the sampling probe 410 or dispensed from the system fluid reservoir 430 through the sampling probe 410. In one embodiment as shown in FIG. 5, the pump 420 may include stepper motor 510 and stepper motor 520 and a syringe 530. The syringe 530 may include a tube 532 and a plunger 534 which is mechanically coupled through a series of gears and a belt (not shown) to the stepper motor 510. Motion of stepper motor 510 causes the plunger 534 to move up or down by a specified number of discrete steps inside the tube 532. The plunger 534 forms a fluid-tight seal with the tube 532. In one embodiment syringe 530 has a usable capacity of 5 mL (though other volumes are possible, e.g., 100 microliter to 25 mL syringes) which is the amount of a system fluid the plunger 534 can displace in one full stroke. Depending on the selected mode of operation, the stepper motor 510 may be capable of making 3,000 or 12,000 discrete steps per plunger 534 full stroke. In one preferred embodiment the stepper motor 510 is directed to make 12,000 steps per full plunger 534 stroke with each step displacing approximately 0.417 microliters of fluid. The pump 420 may include a valve 538 to fluidically couple the sampling probe to the pump, or the valve 538 may be omitted, and a suitable valve, such as valve 440 may be placed in a fluid connection to couple the pump 420 to a sampling probe. A suitable pump for use in the fluid handling system is a CAVRO XLP3000 commercially available from TECAN Ag.

Figure 6:
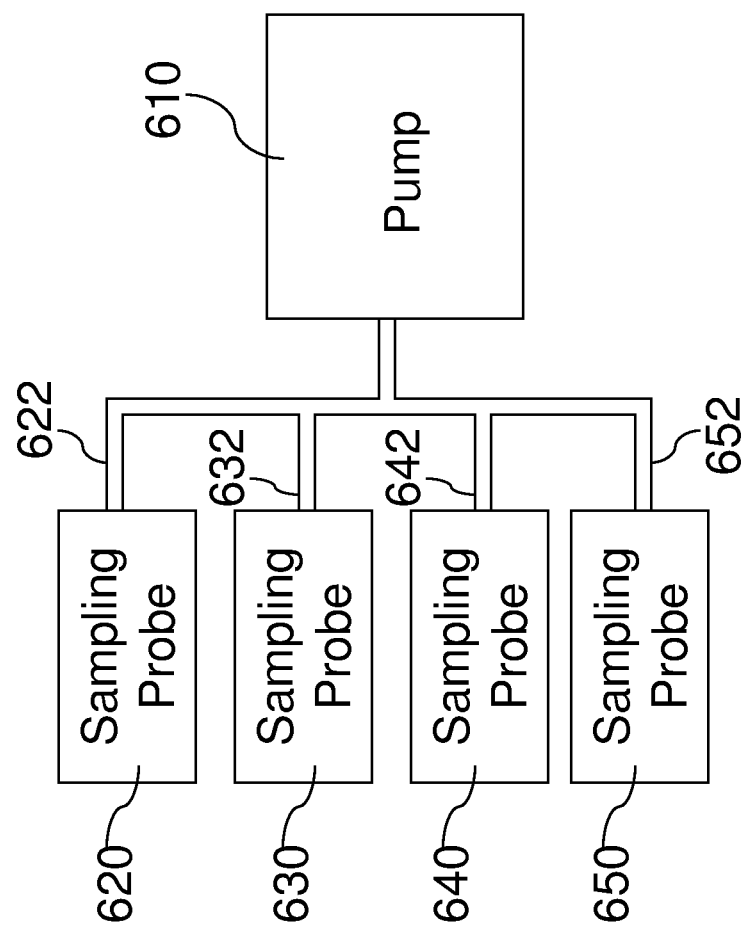
FIG. 6 is an illustration of a single pump fluidically coupled to a plurality of sampling probes, in accordance with certain examples.

In accordance with certain embodiments, to aspirate a fluid using the pump 420, one or more commands from the controller 450 may cause the stepper motor 510 within the pump 420 to aspirate discrete volumes of fluid into the sampling probe 410. The pump 420 may also be used to wash the sampling probe 410 between fluid transfers, and to control the pressure in the system fluid reservoir 430. In some embodiments, the pump 420 may also be used to prime the fluid handling system with fluid from the system fluid reservoir and to dispense aspirated fluid from the sampling probe 410. To prime the fluid handling system 400, the controller 450 may direct the robotic system 460 to position the sampling probe 410 over a wash station contained on the robotic system 460. An initialization control signal may be transmitted to the pump 420 by the controller 450 to causes the valve 440 to rotate connecting the pump 420 and the system fluid reservoir 430. The control signal may also cause the stepper motor 510 to move the plunger 534 to its maximum extent up (Position 1 in FIG. 5) into the tube 532. The next command from the controller 450 causes the stepper motor 510 to move the plunger 534 to its maximum extent down (Position 2 in FIG. 5) inside the tube 532, to extract system fluid from the system fluid reservoir 430. Another command from the controller 450 may direct the valve 440 to rotate again, causing the pump 420 to be fluidically connected with the fluid conduit 435. The next command from the controller 450 to the pump 420 may cause the system fluid inside of the pump 420 to be pushed into the sampling probe 410. Because the fluid handling system 400 typically requires about 10000 milliliters of system fluid to be primed, the sequence of steps described above may be repeated to completely prime the fluid handling system 400. In certain embodiments, a pump may be fluidically coupled to a plurality of sampling probes. An example of this configuration is shown in FIG. 6. A pump 610 is fluidically coupled to sampling probes 620, 630, 640 and 650 through fluid conduits 622, 632, 642 and 652 respectively. One or more valves (not shown) may be included in the fluid conduits such that fluid may be aspirated or dispensed through each of the sampling probes (when the valve is configured to fluidically couple the sampling probe and the pump) or such that less than all of the sampling probes may be used to aspirate and/or dispense fluid (when the valve is configured to disrupt the fluid coupling between the pump and one or more of the sampling probes). In some examples, each sampling probe may be fluidically coupled to the pump 610 through an individual fluid coupling or conduit between the sampling probe and the pump, whereas in other examples a common manifold may fluidically couple the sampling probes to the fluid pump. It will be within the ability of the person of ordinary skill in the art, given the benefit of this disclosure, to choose other suitable methods and devices for fluidically coupling a sampling probe to a pump. In operation of pump 610, the syringe of the pump may be actuated in response to a signal from a controller such that a negative pressure exists at the sampling probe to draw fluid into the sampling probe. To dispense the fluid, another signal may be sent from a controller to cause application of a positive pressure by actuation of the syringe pump such that the fluid is forced out of the sampling probe. In many instances, once fluid is aspirated into the sampling probe, the controller may send a signal to a moveable support to which the sampling probe(s) is coupled. Movement of the moveable support permits dispensing of the fluid into a different container, e.g., microtiter plate, well plate, test tube or the like. Subsequent to dispensing, a system fluid may be dispensed through the sampling probe(s) and into, for example, the same container that the aspirated fluid was dispensed.

Figure 7:
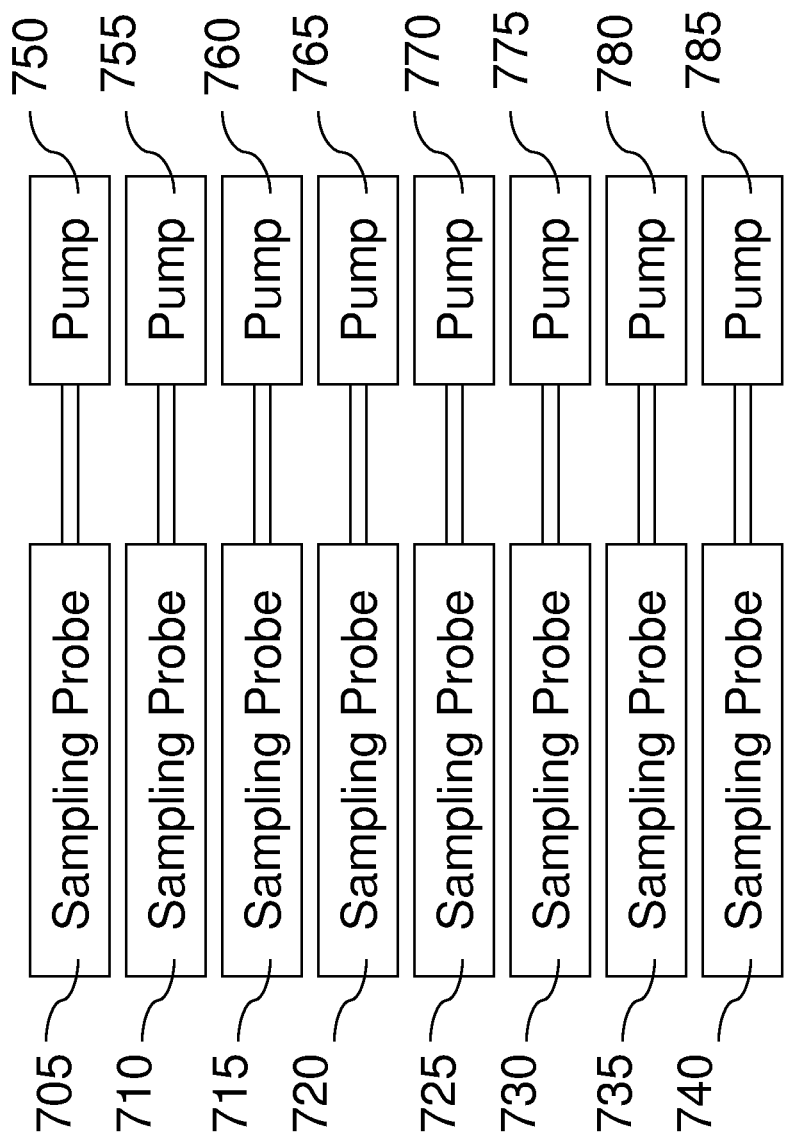
FIG. 7 is an illustration of a plurality of sampling probes each fluidically coupled to its own pump, in accordance with certain examples.
Figure 11:
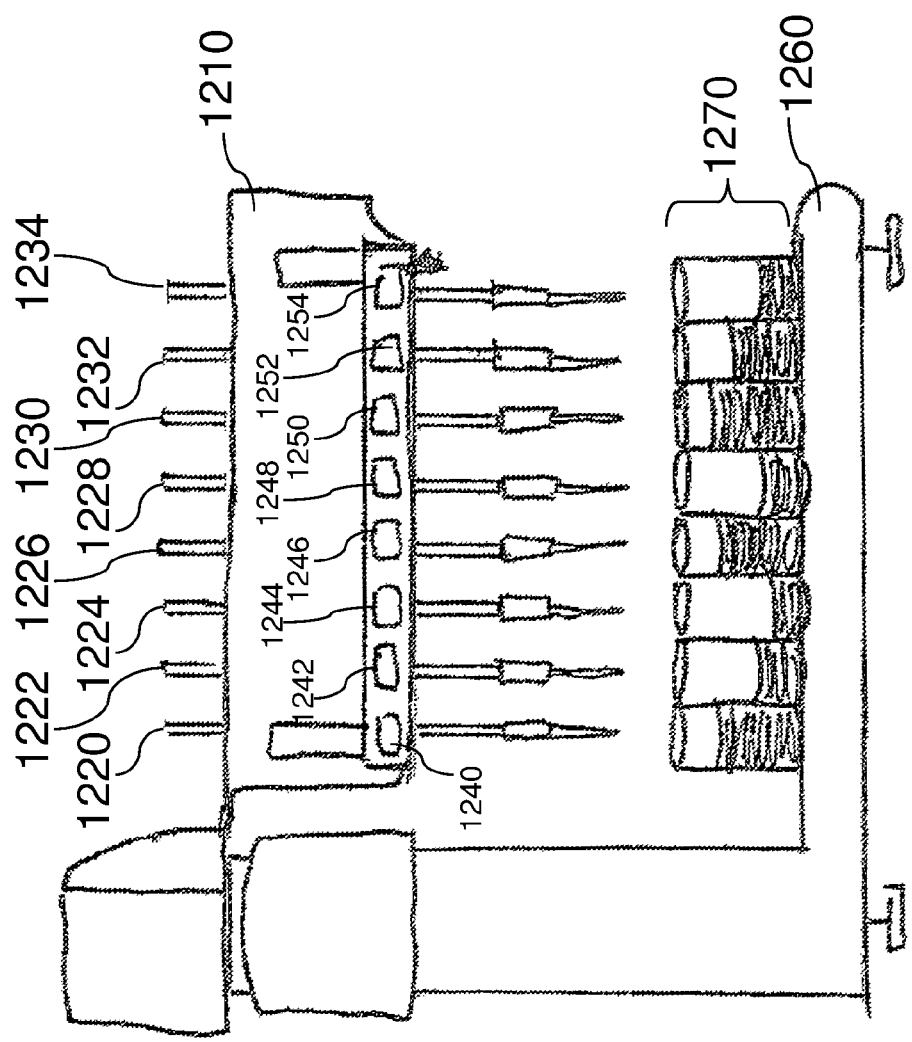
FIG. 11 is side-view illustration of a fluid handling system, in accordance with certain examples.

In other embodiments, each sampling probe may include its own respective pump. An illustration of this configuration is shown in FIG. 7. Sampling probes 705, 710, 715, 720, 725, 730, 735, and 740 are each fluidically coupled to a pump 750, 755, 760, 765, 770, 775, 780 and 785, respectively. In some examples, each of the sampling probes and/or the pump may have an address such that a controller can selectively send signals to one or more of the pumps to aspirate or dispense fluid using the sampling probe fluidically coupled to the pump or pumps that are activated. Such addressing permits the use of one sampling probe, a subset of the sampling probes or all of the sampling probes. In addition, the amount of fluid volume aspirated by any one sampling probe may be selected to be a different volume than any other sampling probe by actuating its respective pump a different amount.

In certain examples, the valve may be configured as a four port valve comprising a L-shaped passage that may fluidically couple two or more ports. For example, the L-shaped passage may fluidically couple the syringe to the sampling probe such that the sampling probe may aspirate or dispense when the syringe moves. By rotation of the L-shaped passage by a selected amount, e.g., ninety degrees, the sampling probe may be coupled to a different port, e.g., a port connected to the system fluid reservoir. For example, the port may be connected to another pump that provides system fluid to the sampling probe, e.g., for priming, flushing or washing. Suitable valves may be obtained, for example, from Tecan on their commercially available Tecan Cavro pumps.

In accordance with certain examples, the system fluid reservoir 430 of the fluid handling systems disclosed herein may include a fluid whose composition and properties are selected depending on the fluid to be sampled. In some examples, the system fluid is selected such that it may be used to wash the sampling probe after fluid has been dispensed from the sampling probe. In some embodiments, the system fluid may be distilled water or an aqueous solution of a detergent or other cleaner. Subsequent to cleaning, the sampling probe may be flushed with distilled water to rinse any remaining cleaner from the sampling probe. In embodiments where the fluid to be sampled is non-aqueous, e.g., is a hydrocarbon such as gasoline or oil, the system fluid may be non-polar as well. For example, where the fluid to be sampled is oil, the system fluid may be kerosene, hexane or other substantially non-polar fluids.

In certain embodiments, the system fluid may be used to dilute the fluid to be sampled such that it is at a suitable concentration or displays suitable properties for analysis. For example, it may be desirable to dilute an opaque sample with a fluid such that the diluted fluid is suitable for optical measurements, e.g., absorbance, fluorescence or other optical measurements. In other embodiments, it may be desirable to dilute the fluid to be sampled such that a reagent in the fluid is present at a desired concentration, e.g., a substrate, an enzyme or the like may be diluted to a suitable concentration prior to analysis using the system fluid. In some embodiments, each of a plurality of sampling probes may aspirate an equivalent volume from a fluid to be sampled, and the different sampling probes may dispense different volumes of fluid such that a standard curve may be generated using the different concentrations produced.

In accordance with certain examples, the robotic system 460 of the moveable support may be configured for movement in 3-axes. The z-axis may be arbitrarily selected to be a vertical axis that is substantially parallel to a long axis of the sampling probe. Measurements by the ultrasound sensor may be used to control how far the moveable support is lowered along the z-axis. The robotic system may be configured to translate the sampling probe in the other directions, e.g., in x- and y-directions to move the sampling probe in directions perpendicular to the z-axis. Illustrative 3-axis robotic systems include those manufactured by Packard Instrument Company (Downers Grove, Ill. and now part of PerkinElmer, Inc. (Waltham, Mass.)), e.g., a MultiPROBE CR10100, and those commonly found in Janus™ systems commercially available from PerkinElmer, Inc.

In accordance with certain embodiments, the fluid handling systems disclosed herein may be configured with a single ultrasound sensor and a plurality of sampling probes. An illustration of this configuration is shown in FIG. 8. The system includes a moveable support 910, an ultrasound sensor 920 and four sampling probes 930, 940, 950, and 960. Each of sampling probes 930, 940, 950 and 960 may independently aspirate and dispense a fluid. In addition, each of the sampling probes 930, 940, 950 and 960 may be fluidically coupled to a system fluid reservoir (not shown). The ultrasound sensor 920 may be positioned on the moveable support or may be positioned, for example, using an outrigger bar as described in reference to FIGS. 1 and 3A-3C. The ultrasound sensor 920 may also be positioned on a track or slide 970 such that it can be translated in a direction perpendicular to a long axis of the sampling probes. Such translation permits the use of the ultrasound sensor to detect a fluid level below each of sampling probes 930, 940, 950 and 960. For example, the ultrasound sensor 920 may be coupled to the sampling probe 930 my positioning the ultrasound sensor 920 at position A on the moveable support 910. Ultrasound energy may be provided to a surface (not shown) below sampling probe 930 and the reflected energy may be used to determine a distance from the sampling probe 930 to a fluid. Subsequent to the distance measurements for sampling probe 930, the ultrasound sensor 920 may be moved to position B to couple the ultrasound sensor 920 to the sampling probe 940. This process may be repeated until distance measurements for each of the sampling probes 930, 940, 950 and 960 have been performed, e.g., by moving the ultrasound sensor to position C and then position D on the moveable support 910. After all distance measurements are made, the different sampling probes 930, 940, 950 and 960 may be independently lowered by a suitable distance such that fluid may be aspirated into each of the sampling probes 930, 940, 950 and 960.

In certain embodiments, the ultrasound sensor 920 may be coupled to a motor configured to move the ultrasound sensor 920 to the various positions along the track 970. The motor may take numerous configurations including, but not limited to, a stepper motor, a linear motor, a piezomotor and the like. Additional suitable motors for moving an ultrasound sensor will be readily selected by the person of ordinary skill in the art, given the benefit of this disclosure. The ultrasound sensor may also be electrically coupled to the controller such that the various data transmitted and received by the ultrasound sensor may be provided to the controller and used to determine the distance any particular sampling probe is from a fluid surface. In some examples, the data provided to the controller is associated with a unique address corresponding to one of the sampling probes such that the data and/or distance calculations for each sampling probe may be added to a list or table. Such list or table may be used to determine how far each sampling probe may be lowered to contact a fluid and/or to aspirate/dispense a fluid.

In accordance with certain examples, the fluid handling systems disclosed herein may be configured with an ultrasound sensor for each of a plurality of sampling probes. An illustration of this configuration is shown in FIG. 9. The system includes a moveable support 1010 and ultrasound sensors 1020, 1025, 1030 and 1035 for sampling probes 1050, 1055, 1060 and 1065, respectively. Each of sampling probes 1050, 1055, 1060 and 1065 may independently aspirate and dispense a fluid. In addition, each of the sampling probes 1050, 1055, 1060 and 1065 may be fluidically coupled to a system fluid reservoir (not shown). The ultrasound sensors 1020, 1025, 1030 and 1035 may be positioned directly on the moveable support or may be positioned, for example, using an outrigger bar as described in reference to FIGS. 1 and 3A-3C. The ultrasound sensor 1020 may be configured to transmit ultrasound energy to, and to receive reflected ultrasound energy from, a surface below the sampling probe 1050. The ultrasound sensor 1025 may be configured to transmit ultrasound energy to, and to receive reflected ultrasound energy from, a surface below the sampling probe 1055. The ultrasound sensor 1030 may be configured to transmit ultrasound energy to, and to receive reflected ultrasound energy from, a surface below the sampling probe 1060. The ultrasound sensor 1035 may be configured to transmit ultrasound energy to, and to receive reflected ultrasound energy from, a surface below the sampling probe 1065. Each of the ultrasound sensors 1020, 1025, 1030 and 1035 may operate independently of the other ultrasound sensors, and ultrasound energy may be transmitted by each of the ultrasound sensors either simultaneously with transmission by other ultrasound sensors or sequentially. By including an ultrasound sensor for each sampling probe, the overall design may be simplified as no additional mechanical parts are needed to move the ultrasound sensor to different positions along the moveable support. Each of the ultrasound sensors 1050, 1055, 1060 and 1065 may provide transmission and reflection data to a controller (not shown) where the data may be used to determine a distance a respective sampling probe should be lowered to contact a fluid and/or to aspirate/dispense a fluid.

In certain examples, the exact spacing between the sampling probes may vary. Illustrative sampling probe spacing is from about 4.5 mm to about 100 mm, more particularly, about 8.5 mm to about 40 mm, e.g., about 8-10 mm. In some embodiments, the ultrasound sensor may be selected such that its energy transmission profile is less than the tip spacing to reduce or avoid interference between ultrasound sensors. For example, where the sampling probes are spaced about 8-10 mm apart, e.g., about 9 mm apart, the ultrasound sensor may be selected such that it transmits energy to detect a surface below its respective sampling probe but does not transmit energy in such a wide pattern that it would interfere with an adjacent ultrasound sensor.

Though the fluid handling system shown in FIGS. 8 and 9 are shown as being configured with four sampling probes, in other embodiments, there may be fewer, e.g., 3, 2 or 1 sampling probes, or more, e.g., at least 5 or at least 8 sampling probes. In addition, two ultrasound sensors may be used with more than two sampling probes, e.g., with four sampling probes, such that each of the sensors may be positioned above one or more sampling probes at different times. Similarly, four ultrasound sensors may be used with more than four sampling probes, e.g., eight sampling probes, such that one or more of the ultrasound sensors may be moveable and provide ultrasound data for two or more of the sampling probes. Additional configurations that use fewer ultrasound sensors than sampling probes will be readily selected by the person of ordinary skill in the art, given the benefit of this disclosure.

In accordance with certain examples, the controller of the fluid handling system may include one or more algorithms. The algorithm may be designed to receive input from one or more ultrasound sensors, determine a distance to a fluid surface using the input and provide an output that causes movement of the sampling probe vertically by a distance sufficient to lower the sampling probe into the fluid to be sampled. In some examples, a list may be generated by the algorithm such that distances are written to the list, and the list is subsequently read by the software to cause movement of the sampling probes. In instances where the ultrasound measurements are not needed, the software may ignore the list or read the list with no entries and move the sampling probes based on user input instead of distance calculations based on ultrasound data. Illustrative software suitable for use with the fluid handling systems disclosed herein includes, but is not limited to, the WinPrep® software available with the Janus™ systems that are commercially available from PerkinElmer, Inc. (Waltham, Mass.).

In some examples, the controller may also be configured to control movement of a fluid container on a surface of the fluid handling system. For example, it may be desirable to move the fluid container relative to the position of the sampling probe to facilitate ultrasound measurements and aspiration of the fluid from the sampling probe. The fluid container may be moved in three dimensions or, in certain examples, the fluid container may be moved in two dimensions or in one dimension. Illustrative fluid containers include, but are not limited to, microtiter plates, well plates, test tubes, Eppendorf® tubes, conical vials, centrifuge tubes, cryogenic vials, beakers, round bottom flasks and the like. In some examples, the fluid container may be placed on a surface configured to retain the fluid container through, for example, insertion of the base of the fluid container into an aperture or slot.

In accordance with certain examples, the sampling probes for use in the fluid handling systems disclosed herein may include a detachable or removable sampling element fluidically coupled to the bottom of the sampling probe. This sampling element is the site where fluid is aspirated and dispensed. By aspirating the fluid into the sampling element, the body of the sampling probe does not contact the fluid, which could result in contamination of the sampling probe. In some examples, the sampling element may be attached to the sampling probe by friction fitting of the sampling probe body to the sampling element. Such fitting may be performed automatically by movement of the sampling probe in the z-axis direction to contact the sampling element with sufficient force to cause retention of the sampling element by the sampling probe. The sampling probe/element may then be moved to a different location for ultrasound transmission by the ultrasound sensor prior to aspiration of a fluid into the sampling element. Illustrative materials for use in the sampling element include, but are not limited to, polymers, plastics, polytetrafluoroethylene and other materials that generally are non-reactive towards most fluids or solvents. Illustrative volume capacities for the sampling elements may vary from about 1 microliter to about 10 milliliters.

In certain examples, after aspiration and dispensing of the fluid, the sampling element(s) may be washed by aspirating a fluid into the sampling element or by flushing fluid from the system fluid reservoir through the sampling element(s) prior to reuse. In other examples, the sampling element may be used once and then detached or ejected from the sampling probe. For example, one or more parallel rods may be mounted adjacent to the sampling probe body. While the rod is fixed, the sampling probe may be moved vertically, and upon contacting of the rod by the sampling element, the sampling element is ejected. In some examples, each sampling probe may have a respective rod mounted adjacent to it such that either all sampling elements may be ejected at the same time or the individual sampling probes may be controlled such that fewer than all the sampling elements are ejected. In certain examples, it may be desirable to eject the sampling elements prior to dispensing of a system fluid through the sampling probe such that the system fluid may be dispensed more rapidly.

In accordance with certain examples, additional components may also be included in the fluid handling systems disclosed herein including, for example, status lights to indicate an operating status, e.g., whether an ultrasound sensor is on or off, pressure control systems, gripper arms, additional robotic arms and the like. Illustrative additional components such as, for example, pressure control systems are described in commonly assigned U.S. Pat. Nos. 6,079,283, 6,203,759 and 6,537,817, each of which is hereby incorporated herein by reference. Additional components for including in the fluid handling systems will be readily selected by the person of ordinary skill in the art, given the benefit of this disclosure.

In accordance with certain examples, a method that uses an ultrasound sensor to sample a fluid is provided. In some examples, a distance from a sampling probe to a fluid surface may be determined and used to lower the sampling probe an effective distance into a fluid. In some examples, the distance may be determined by providing ultrasound energy from an ultrasound sensor to the fluid surface of a fluid in a fluid container, and receiving reflected ultrasound energy from the fluid surface using the ultrasound sensor to determine the distance between the sampling probe and the fluid surface. Once the distance is known, the sampling probe may be lowered an effective distance into the fluid to aspirate a selected volume of fluid from the fluid container into the sampling probe. Subsequent to aspiration, the fluid may be dispensed into another fluid container.

In certain embodiments, the method may further comprise providing ultrasound energy to a surface configured to receive the fluid container and receiving reflected ultrasound energy using the ultrasound sensor to determine a distance from the sampling probe to the surface. This step may be used, for example, to determine the distance the sampling probe is from a surface designed to receive a fluid container or may be used in one or more calibration steps. However, if the distance from a start or initial position of the sampling probe to the surface is known, then the device can reset itself to this position prior to any ultrasound measurements and this step may be omitted. Even if the distance to the surface is known, it may be desirable to perform this step to ensure the device has not strayed from its zero position. In some examples, the method may further include dispensing a system fluid from a system fluid reservoir fluidically coupled to the sampling probe through the sampling probe. Such dispensing of a system fluid may be used, for example, to flush the sampling probe, to dilute the dispensed sample or may be used for other purposes.

In accordance with certain embodiments, a method of sampling a hydrocarbon fluid to minimize a depth at which a sampling probe is lowered into the hydrocarbon fluid is disclosed. As discussed herein, it may be desirable to minimize how much of the outer surface of a sampling element contacts a hydrocarbon fluid, as a hydrocarbon fluid may adhere or otherwise adsorb to the outer surface of the sampling element, which can lead to volume inaccuracies and decrease the precision of the fluid handling system. An illustration of this sampling is shown in FIGS. 10A and 10B. In FIG. 10A, a sampling probe 1110 has been lowered into a fluid 1120 to a distance much lower than is needed to aspirate a selected volume of the fluid 1120 into the sampling probe 1110. This increased lowering results in an increased amount of the sampling probe 1110 outer surface that contacts the fluid 1120, which increases the likelihood that the fluid 1120 may adhere or adsorb to the outer surface of the sampling probe 1110. During dispensing, the fluid adhered to the outer surface may drip off due to gravitational forces or movement of the sampling probe. This dripping can lead to inaccuracies in the sampled volume. Referring to FIG. 10B, a sampling probe 1150 has been lowered a minimum distance into a fluid 1160 such that a selected amount of volume can be aspirated into the sampling probe 1150 while minimizing or reducing the amount of outer surface of the sampling probe 1150 that is exposed to the fluid 1160.

In certain examples, the exact minimum distance used to lower the sampling probe 1150 into the fluid 1160 may vary with the amount of fluid to be aspirated. In some examples, it may be desirable to aspirate a portion of the selected volume and then lower the sampling probe into the fluid further such that the amount of outer surface contacting the fluid is minimized. For example, about 0.25 mL of fluid may be aspirated into the sampling probe, the sampling probe may be lowered and another 0.25 mL may be aspirated, and this process may be repeated until a desired total volume has been aspirated into the sampling probe. In an alternative method, the sampling probe may be lowered at a fixed rate as fluid is being aspirated such that fluid is continuously drawn into the sampling probe as the sampling probe is lowered. Additional methods of sampling a fluid while minimizing or reducing the amount of sampling probe surface contacting a fluid will be readily selected by the person of ordinary skill in the art, given the benefit of this disclosure.

In certain examples, the hydrocarbon fluid may be sampled by determining a distance from a sampling probe to the hydrocarbon fluid surface by providing ultrasound energy from an ultrasound sensor to the hydrocarbon fluid surface in a fluid container, and receiving reflected ultrasound energy from the hydrocarbon fluid surface using the ultrasound sensor to determine the distance between the sampling probe and the hydrocarbon fluid surface. These measurements may be used to determine or calculate a sampling distance to lower the sampling probe into the hydrocarbon fluid to aspirate a selected volume of fluid from the hydrocarbon fluid in the sampling probe. The sampling distance may be selected such that a selected volume of fluid is aspirated while minimizing a depth at which the sampling probe is lowered into the hydrocarbon fluid.

In accordance with certain examples, similar methods as those described above in reference to hydrocarbon fluids may be used for sampling of non-viscous and viscous fluids such as the illustrative non-viscous and viscous fluids described herein.

Certain specific examples are described below to illustrate further the novel technology described herein.

EXAMPLE 1

Microliter quantities of an aqueous solution may be sampled using a fluid handling system. The fluid handling system may include an ultrasound sensor and a sampling probe each attached to a moveable support. A pump is coupled to the sampling probe to aspirate and/or dispense fluid through the sampling probe. A controller is electrically coupled to the ultrasound sensor and moveable support. The ultrasound sensor transmits ultrasound energy to a fluid under the sampling probe. The ultrasound sensor also receives reflected energy from the fluid surface and provides such data to the controller. A distance between the sampling probe and the fluid surface is determined by the controller. A signal is sent to the moveable support to lower the sampling probe a suitable distance into the fluid. About 10-20 microliters is aspirated into the sampling probe using the pump. A signal is sent by the controller to the moveable support to raise the moveable support and thus raise the sampling probe. The aspirated fluid may be dispensed on or in a second fluid container such as, for example, a test tube, a slide or a well plate.

EXAMPLE 2

A fluid handling system may be used to produce an array of material disposed on a substrate. The fluid handling system may include four or more sampling probes each coupled to its own ultrasound sensor. In certain configurations, however, a single ultrasound sensor may be used with all of the sampling probes. In this example with multiple ultrasound sensors, each of the ultrasound sensors and each of the sampling probes is coupled to a moveable support. A pump is coupled to each sampling probe to aspirate and dispense fluid through the sampling probe. A controller is electrically coupled to each of the ultrasound sensors and the moveable support. Each of the ultrasound sensors transmits ultrasound energy to a fluid under its respective sampling probe. The ultrasound sensors also receive reflected energy from the fluid surfaces and provide such data to the controller. The distance between each sampling probe and the fluid surface of the fluid under each sampling probe is determined by the controller. A signal is sent to the moveable support to lower the sampling probe a suitable distance into the fluid. If the distances to the fluid surface differ for different sampling probes, then different signals may be sent such that the different sampling probes may be lowered by different distances. About 125-150 microliters is aspirated into each of the sampling probes using the pump fluidically coupled to each of the sampling probes. A signal is sent by the controller to the moveable support to raise the moveable support and thus raise the sampling probes. The moveable support may be placed over a glass slide or a microtiter plate, and aliquots from each sampling probe may be dispensed onto the glass slide or microtiter plate to provide an array. For example, 96 spots of 5 microliters each may be spotted onto the glass slide to provide an array, e.g., an array of biological molecules. In an alternative array, 5 microliters may be dispensed into each well of a microtiter plate to provide an array.

EXAMPLE 3

A fluid handling system that includes eight sampling probes each coupled to an ultrasound sensor is shown in FIG.

11. The fluid handling system 1200 includes a robotic arm 1210, a plurality of sampling probes 1220-1234 each with its own respective ultrasound sensor 1240-1254. The fluid handling system also include a surface 1260 configured to receive fluid containers, such as fluid containers collectively shown as element 1270. Each of the sampling probes is also fluidically coupled to a system fluid reservoir (not shown).

Figure 12:
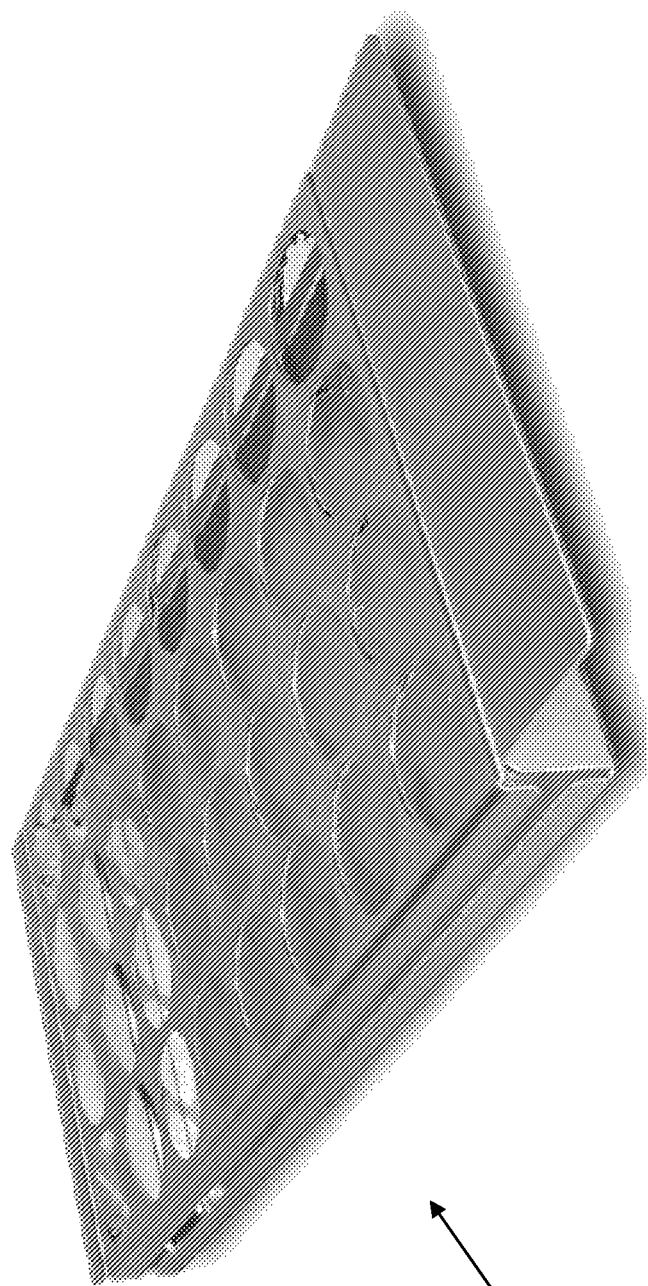
FIG. 12 is a perspective view of a sample rack, in accordance with certain examples.

In one illustration, the robotic arm 1210 is initially positioned in a "park" position over the surface 1260. The ultrasound sensors 1240-1254 are first calibrated by detecting a distance to the surface 1260. In the park position, the distance between the ultrasound sensors 1240-1254 and the surface 1260 is about 150 mm. Containers 1270 may be as tall as 145 mm or may be significantly smaller. In this example, the fluid containers may be large mouth bottles having a height of 55 mm. Each of the bottles may rest in a sample rack 1300 as shown in FIG. 12. The fluid level in each of fluid containers 1270 is detected by transmitting ultrasound energy and receiving reflected ultrasound energy in the fluid containers 1270. In this illustration, the fluid containers 1270 contain oil samples. After detection of the fluid levels, sampling elements (1 mL pipette tips) are attached to the sampling probes 1220-1234 using friction fitting of the sampling probe bodies to the sampling elements. Each of the sampling probes/elements is lowered a suitable distance into the fluid and 500 microliters of sample is then aspirated into the sampling elements. The robotic arm 1210 then raises the sampling probe and moves the sampling probe over eight test tubes positioned in a row. The 500 microliters of aspirated fluid is then dispensed into the test tubes, and the sampling elements are ejected from the sampling probes. 4.5 mL of a system fluid (kerosene) is then dispensed through the sampling probes and into each test tube. The sampling probes are raised as the system fluid is dispensed into each test tubes. After dispensing of the system fluid, the sampling probes 1220-1234 are dipped into a wash station to remove any residual fluids from their surfaces.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples may be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A device, comprising:
    a plurality of sampling probes configured to sample a fluid;
    an ultrasound sensor coupled to the plurality of sampling probes, the ultrasound sensor configured to be moveable and to be used with each of the plurality of sampling probes, the ultrasound sensor further configured to:
        transmit and receive ultrasound energy;
        generate a first signal by receiving ultrasound energy reflected from a fluid surface of the fluid; and
        generate a second signal by detecting ultrasound energy reflected from a first surface configured to receive a fluid container comprising the fluid; and
    a controller electrically coupled to the ultrasound sensor and the plurality of sampling probes, the controller configured to receive the first signal and the second signal from the ultrasound sensor, and further configured to provide a control signal to each of the plurality of sampling probes to control a distance each of the plurality of sampling probes is lowered into the fluid based on the first signal, the second signal and a selected fluid volume to be sampled.

2. The device of claim 1, further comprising a plurality of ultrasound sensors, wherein one of the plurality of sampling probes is configured for use with one of the plurality of ultrasound sensors.

* * * * *